United States Patent

Fukami et al.

[11] Patent Number: 6,043,246
[45] Date of Patent: Mar. 28, 2000

[54] UREA DERIVATIVES

[75] Inventors: Takehiro Fukami; Takahiro Fukuroda; Akio Kanatani; Masaki Ihara, all of Tsukuba, Japan

[73] Assignee: Banyu Pharmaceutical Co., Ltd., Tokyo, Japan

[21] Appl. No.: 09/308,668

[22] PCT Filed: Dec. 2, 1997

[86] PCT No.: PCT/JP97/04399

§ 371 Date: Jul. 26, 1999

§ 102(e) Date: Jul. 26, 1999

[87] PCT Pub. No.: WO98/24768

PCT Pub. Date: Jun. 11, 1998

[30] Foreign Application Priority Data

Dec. 3, 1996 [JP] Japan .................... 8-337593

[51] Int. Cl.[7] ............ A61K 31/415; A61K 31/496; C07D 231/40; C07D 403/12
[52] U.S. Cl. ............ 514/252; 514/404; 540/575; 544/364; 544/371; 548/371.7; 546/211; 546/275.4
[58] Field of Search .............. 548/371.7; 544/371, 544/364; 514/404

[56] References Cited

U.S. PATENT DOCUMENTS 4,089,962  5/1978  Harrison et al. .

FOREIGN PATENT DOCUMENTS

| 51-146465 | 12/1976 | Japan . |
| 2-300173 | 12/1990 | Japan . |
| 3-93774 | 4/1991 | Japan . |
| WO 96/14843 | 5/1996 | WIPO . |
| WO 99/27965 | 6/1999 | WIPO . |

Primary Examiner—Robert W. Ramsuer
Attorney, Agent, or Firm—Oblon, Spivak, McClelland, Maier & Neustadt, PC

[57] ABSTRACT

The present invention relates to a compound represented by the general formula [I]:

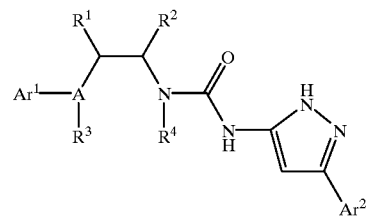

wherein A represents a nitrogen atom or a group represented by C—$R^5$; $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ represents a hydrogen atom, a lower alkyl group or a bond formed by linking to $R^5$; $R^2$ represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a hydroxyl, lower alkyl or lower alkoxy group or a bond formed by linking to $R^1$, or its salt, a process for its preparation and an agent for the treatment of bulimia, obesity or diabetes comprising it as an active ingredient.

12 Claims, No Drawings

UREA DERIVATIVES

This application is a 371 of PCT/JP97/04399 filed Dec. 2, 1997.

FIELD OF THE INVENTION

The present invention is useful in the field of medicines. More specifically, novel pyrazole derivatives of the present invention are useful as neuropeptide Y receptor antagonists and as agents for the treatment of various diseases of circulatory organs, central nervous system and metabolic system.

BACKGROUND OF THE INVENTION

Neuropeptide Y (to be referred to as NPY hereinafter) is a peptide consisting of 36 amino acids, which was isolated from porcine brain for the first time by Tatemoto et al. in 1982 [Nature, vol.296, p.659 (1982)]. NPY is broadly distributed in central nervous and peripheral nervous systems and has various in vivo functions as one of the peptides most abundantly present in the nervous system. That is, in the central nervous system, NPY acts as an aperitive and significantly promotes a fat accumulation via secretion of various hormones and actions of the nervous system. It is known that a continuous intracerebroventricular administration of NPY induces obesity and insulin resistance based on the above actions. NPY is also associated with the control of mood and functions of the central autonomic nervous system. In addition, in the peripheral nervous system, NPY is present together with norepinephrine in the sympathetic nerve terminal and associated with the tension of the sympathetic nervous system. It is known that a peripheral administration of NPY causes vasoconstriction and enhances actions of other vasoconstrictors including norepinephrine [International Journal of Obesity, vol.19, p.517 (1995); Endocrinology, vol.133, p.1753 (1993); British Journal of Pharmacology, vol.95, p.419 (1988)].

The function of NPY is expressed when it is bound to an NPY receptor present in the central or peripheral nervous system. Therefore, the expression of the function of NPY can be prevented if the binding of NPY to the NPY receptor is inhibited. Consequently, it is expected that compounds capable of inhibiting the binding of NPY to the NPY receptor are useful in the prevention or treatment of various diseases associated with NPY, for example, diseases of circulatory organs such as hypertension, nephropathy, cardiopathy and angiospasm; diseases of central nervous system such as bulimia, depression, epilepsy and dementia; metabolic diseases such as obesity, diabetes and dysendocrisiasis, or glaucoma [Trends in Pharmacological Sciences, vol.15, p.153 (1994)].

Compounds structurally similar to the compounds of the present invention are disclosed in International Publication WO 96/14843, JP 3093774A, JP 2300173A, JP 51146465A and etc. However, these publications do not clearly disclose nor suggest the compound of the present invention. And, an antagonistic action to NPY is not described at all therein.

DISCLOSURE OF THE INVENTION

An object of the present invention is to provide a new medicine having an antagonistic action to NPY.

The present inventors have found that a compound represented by the general formula [I]:

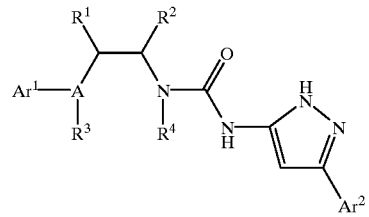

[I]

wherein A represents a nitrogen atom or a group represented by C—$R^5$; $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ represents a hydrogen atom, a lower alkyl group or a bond formed by linking to $R^5$; $R^2$ represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a hydroxyl, lower alkyl or lower alkoxy group or a bond formed by linking to $R^1$, has an antagonistic action to NPY.

Since the compound [I] of the present invention has an antagonistic action to NPY, it is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma.

Especially, the compound [I] of the present invention is useful as an agent for the treatment of bulimia, obesity, diabetes or the like.

The present invention relates to a compound represented by the general formula [I] or its salt as well as a method for its preparation and its use.

Symbols and terms as used herein are described below.

The term "halogen atom" as used herein means fluorine, chlorine, bromine or iodine.

The term "lower alkyl group" as used herein means a straight, branched or cyclic alkyl group containing 1 to 7 carbon atoms, and its illustrative examples include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, cyclopropyl, cyclobutyl, cyclopentyl, cyclohexyl, cycloheptyl, cyclopropylmethyl, 1-cyclopropylethyl, 2-cyclopropylethyl, 1-cyclopropylpropyl, 2-cyclopropylpropyl, 3-cyclopropylpropyl, cyclopentylmethyl, 2-cyclopentylethyl and cyclohexylmethyl and the like.

The term "lower haloalkyl group" as used herein means the above lower alkyl group comprising the aforementioned halogen atom, and its illustrative examples include fluoromethyl, difluoromethyl, trifluoromethyl, 1-fluoroethyl, 2-fluoroethyl, 2,2,2-trifluoroethyl, pentafluoroethyl, chloromethyl, dichloromethyl, trichloromethyl, 1-chloroethyl and 2-chloroethyl and the like.

The term "aryl group" as used herein means phenyl, naphthyl or anthryl, of which phenyl and naphthyl are preferred.

The term "lower alkenyl group" as used herein means a straight or branched alkenyl group containing 2 to 7 carbon atoms, and its illustrative examples include vinyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl and the like.

The term "lower alkoxy group" as used herein means an alkoxy group comprising the aforementioned lower alkyl group, namely an alkoxy group containing 1 to 7 carbon atoms, or an alkylenedioxy group containing 1 to 3 carbon atoms, and its illustrative examples include methoxy, ethoxy, propyloxy, isopropyloxy, butoxy, isobutyloxy, tert-butoxy, pentyloxy, cyclopropyloxy, cyclobutyloxy, cyclopentyloxy, cyclohexyloxy, cycloheptyloxy, cyclopropylmethyloxy, 1-cyclopropylethyloxy, 2-cyclopropylethyloxy, 1-cyclopropylpropyloxy, 2-cyclopropylpropyloxy, 3-cyclopropylpropyloxy, cyclopentylmethyloxy, 2-cyclopentylethyloxy, cyclohexylmethyloxy, methylenedioxy, ethylenedioxy and trimethylenedioxy and the like.

The term "lower alkylthio group" as used herein means an alkylthio group comprising the aforementioned lower alkyl group, namely an alkylthio group containing 1 to 7 carbon atoms, and its illustrative examples include methylthio, ethylthio, propylthio, isopropylthio, butylthio, isobutylthio, tert-butylthio, pentylthio, cyclopropylthio, cyclobutylthio, cyclopentylthio, cyclohexylthio, cycloheptylthio, cyclopropylmethylthio, 1-cyclopropylethylthio, 2-cyclopropylethylthio, 1-cyclopropylpropylthio, 2-cyclopropylpropylthio, 3-cyclopropylpropylthio, cyclopentylmethylthio, 2-cyclopentylethylthio and cyclohexylmethylthio and the like.

The term "lower alkylamino group" as used herein means an amino group monosubstituted with the aforementioned lower alkyl group, and its illustrative examples include methylamino, ethylamino, propylamino, isopropylamino, butylamino, sec-butylamino and tert-butylamino and the like.

The term "lower dialkylamino group" as used herein means an amino group disubstituted with the aforementioned lower alkyl group, and its illustrative examples include dimethylamino, diethylamino, ethylmethylamino, dipropylamino, methylpropylamino and diisopropylamino and the like.

The term "heteroaryl group" as used herein means a 5- or 6-membered monocyclic aromatic heterocyclic ring group containing 1 or more, preferably 1 to 3, of heteroatoms which may be the same or different and are selected from the group consisting of oxygen, nitrogen and sulfur, or a condensed aromatic heterocyclic ring group in which said monocyclic aromatic heterocyclic ring group and the aforementioned aryl group are condensed or in which the same or different members of said monocyclic aromatic heterocyclic ring groups are mutually condensed, and its illustrative examples include pyrrolyl, furyl, thienyl, imidazolyl, pyrazolyl, thiazolyl, isothiazolyl, oxazolyl, isoxazolyl, triazolyl, oxadiazolyl, thiadiazolyl, pyridyl, pyrazinyl, pyrimidinyl, pyridazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthylidinyl, quinoxalinyl, quinazolinyl, cinnolinyl and pteridinyl and the like.

The term "alkylene group containing 2 to 4 carbon atoms" as used herein means a straight chain alkylene group, namely ethylene, trimethylene or tetramethylene.

The "salt" of the compound represented by the general formula [I] means any conventional pharmaceutically acceptable salt, and its examples include acid addition salts based on basic groups such as a basic heterocyclic ring group or an amino substituents and the like.

Illustrative examples of the acid addition salt include an inorganic salt such as hydrochloride, sulfate, nitrate, phosphate and perchlorate; an organic salt such as maleate, fumarate, tartarate, citrate, ascorbate and trifluoroacetate; and sulfonate such as methanesulfonate, isethionate, benzenesulfonate and p-toluenesulfonate.

The term "agent for the treatment" as used herein means a drug to be used for the treatment and/or prevention of various diseases.

Various symbols in the general formula [I] are described further in detail with reference to its preferred embodiment in order to explain the compound represented by the above general formula [I] of the present invention more clearly.

"A" means nitrogen atom or a group represented by C—$R^5$.

Nitrogen atom is preferred as "A".

$Ar^1$ means an aryl group which may have a substituent selected from the group consisting of a halogen atom and lower alkyl and lower haloalkyl groups.

The term "an aryl group which may have a substituent selected from the group consisting of a halogen atom and lower alkyl and lower haloalkyl groups" means the aforementioned aryl group unsubstituted or substituted at any substitutable position with 1 or more, preferably 1 or 2, substituents which may be the same or different and are selected from the group consisting of a halogen atom and lower alkyl and lower haloalkyl groups.

Preferred examples of the halogen atom as said substituent include chlorine and bromine.

Preferred examples of the lower alkyl group as said substituent include methyl, ethyl, propyl, isopropyl, cyclopropyl, butyl, isobutyl, sec-butyl, tert-butyl and pentyl, of which methyl, ethyl, propyl, isopropyl and cyclopropyl are more preferred.

Preferred examples of the lower haloalkyl group as said substituent include trifluoromethyl.

The said substituent is preferably a halogen atom.

Preferred examples of the aryl group as $Ar^1$ include phenyl.

In consequence, preferred examples of $Ar^1$ include phenyl and 3-chlorophenyl, of which 3-chlorophenyl is more preferred.

$Ar^2$ means an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups.

The term "an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups" means the aforementioned aryl or heteroaryl group unsubstituted or substituted at any substitutable position with 1 or more, preferably 1 or 2, substituents which may be the same or different and are selected from the group consisting of a halogen atom and lower alkyl, lower alkenyl, lower haloalkyl, lower alkoxy, lower alkylthio, lower alkylamino, lower dialkylamino and aryl groups.

Preferred examples of the halogen atom as said substituent include chlorine and bromine.

Preferred examples of the lower alkyl group as said substituent include methyl and ethyl.

Preferred examples of the lower alkenyl group as said substituent include vinyl, 2-propenyl, isopropenyl, 2-butenyl and 3-methyl-2-butenyl, of which vinyl and 2-propenyl are more preferred.

Preferred examples of the lower haloalkyl group as said substituent include fluoromethyl and trifluoromethyl.

Preferred examples of the lower alkoxy group as said substituent include methoxy, ethoxy, propyloxy and methylenedioxy of which methoxy and methylenedioxy are more preferred.

Preferred examples of the lower alkylthio group as said substituent include methylthio, ethylthio and propylthio, of which methylthio is more preferred.

Preferred examples of the lower alkylamino group as said substituent include methylamino.

Preferred examples of the lower dialkylamino group as said substituent include dimethylamino.

Preferred examples of the aryl group as said substituent include phenyl.

As said substituent, a halogen atom and a lower alkyl, lower alkoxy, lower alkylthio or lower dialkylamino group are preferred.

Preferred examples of the aryl group as $Ar^2$ include phenyl, and those of the heteroaryl group include pyridyl.

In consequence, preferred examples of $Ar^2$ include phenyl, 1-naphthyl, 2-naphthyl, 2-pyridyl, 3-pyridyl, 4-pyridyl, 2-chlorophenyl, 3-chlorophenyl, 4-chlorophenyl, 3,4-dichlorophenyl, 2-bromophenyl, 3-bromophenyl, 4-bromophenyl, 5-chloro-3-pyridyl, 5-bromo-3-pyridyl, 2-methylphenyl, 3-methylphenyl, 4-methylphenyl, 3-ethylphenyl, 4-ethylphenyl, 4-propylphenyl, 5-methyl-2-pyridyl, 6-methyl-3-pyridyl, 6-ethyl-3-pyridyl, 2-methyl-4-pyridyl, 2-ethyl-4-pyridyl, 2-propyl-4-pyridyl, 2-butyl-4-pyridyl, 3-methyl-4-pyridyl, 3-vinylphenyl, 4-vinylphenyl, 4-(2-propenyl)phenyl, 5-vinyl-3-pyridyl, 3-trifluoromethylphenyl, 4-trifluoromethylphenyl, 2-methoxyphenyl, 3-methoxyphenyl, 4-methoxyphenyl, 4-ethoxyphenyl, 4-isopropyloxyphenyl, 3,4-dimethoxyphenyl, 3,4-methylenedioxyphenyl, 6-methoxy-3-pyridyl, 2-methoxy-4-pyridyl, 3-dimethylaminophenyl, 4-dimethylaminophenyl, 4-methoxy-3-dimethylaminophenyl, 2-methylthiophenyl, 3-methylthiophenyl, 4-methylthiophenyl, 2-methylthio-4-pyridyl, 3-biphenylyl and 4-biphenylyl, of which 4-pyridyl, 2-methyl-4-pyridyl, 2-ethyl-4-pyridyl, 2-propyl-4-pyridyl, 2-butyl-4-pyridyl, 3-chlorophenyl, 4-chlorophenyl, 3,4-dichlorophenyl, 3-bromophenyl, 4-bromophenyl, 2-methylphenyl, 3-methylphenyl, 4-methylphenyl, 4-ethylphenyl, 3-methyl-4-pyridyl, 3-ethyl-4-pyridyl, 4-vinylphenyl, 4-(2-propenyl)phenyl, 3-methoxyphenyl, 4-methoxyphenyl, 4-ethoxyphenyl, 3,4-dimethoxyphenyl, 3,4-methylenedioxyphenyl, 3-methoxy-4-pyridyl, 4-methylthiophenyl and 3-methylthio-4-pyridyl are more preferred.

$R^1$ means a hydrogen atom, a lower alkyl group or a bond formed by linking to $R^5$.

Preferred examples of the lower alkyl group as $R^1$ include methyl and ethyl.

The term "a bond formed by linking to $R^5$" means that, when A is a group represented by C—$R^5$, $R^1$ and $R^5$ are linked to each other to form a double bond together with the existing bond.

Preferred as $R^1$ is hydrogen or a bond formed by linking to $R^5$.

$R^2$ means a hydrogen atom or a lower alkyl group.

Preferred examples of the lower alkyl group as $R^2$ include methyl and ethyl.

Hydrogen is preferred as $R^2$.

$R^3$ and $R^4$ may be the same or different and each means a hydrogen atom or a lower alkyl group, or $R^3$ and $R^4$ are linked to each other to form an alkylene group containing 2 to 4 carbon atoms which may have a lower alkyl group.

Preferred examples of the lower alkyl group as $R^3$ and $R^4$ include methyl and ethyl.

The term "an alkylene group containing 2 to 4 carbon atoms which may have a lower alkyl group" means the aforementioned alkylene group unsubstituted or substituted at any substitutable position with 1 or more of the aforementioned lower alkyl groups which may be the same or different, of which the unsubstituted alkylene group is preferred.

Preferred examples of the lower alkyl group as the substituent include methyl, ethyl, propyl and isopropyl, of which methyl is more preferred.

Preferred examples of $R^3$ and $R^4$ include a lower alkyl group which may be the same or different, and an alkylene group containing 2 to 4, particularly 2, carbon atoms which is formed by linking $R^3$ and $R^4$ and which may have a lower alkyl group.

$R^5$ means a hydrogen atom, a hydroxyl, lower alkyl or lower alkoxy group or a bond formed by linking to $R^1$.

Preferred examples of the lower alkyl group as $R^5$ include methyl and ethyl.

Preferred examples of the lower alkoxy group as $R^5$ include methoxy, ethoxy and propyloxy.

The term "a bond formed by linking to $R^1$" means that, when A is a group represented by C—$R^5$, $R^1$ and $R^5$ are linked to each other to form a double bond together with the existing bond.

Preferred as $R^5$ is hydrogen, hydroxyl or a bond formed by linking to $R^1$.

Depending on the nature of substituent, the compounds of the present invention may exist in various stereoisomers including optical isomers, diasteromers and geometrical isomers, and tautomers. All of these stereoisomers and tautomers and their mixtures are also included in the present invention.

In this connection, in order to avoid unnecessary confusion in naming each of the compounds of the present invention, position numbers of the pyrazole ring moiety of the compound represented by the general formula [I] are defined as shown in the following general formula [I'], and the nomenclature and other explanations of each compound are described based on this formula.

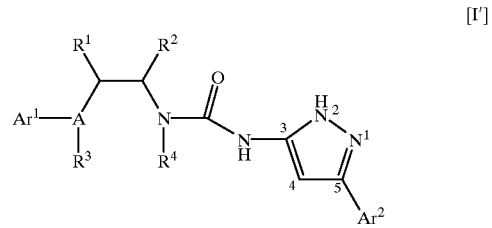

Illustrative examples of the compound represented by the general formula [I] include:
5-(4-methoxyphenyl)-3-(4-phenylpiperazinyl) carbonylaminopyrazole, 5-(4-chlorophenyl)-3-(4-phenylpiperazinyl)
carbonylaminopyrazole,
5-(2-methylphenyl)-3-(4-phenylpiperazinyl)
carbonylaminopyrazole,
5-(3-methylphenyl)-3-(4-phenylpiperazinyl)
carbonylaminopyrazole,
5-(4-methylphenyl)-3-(4-phenylpiperazinyl)
carbonylaminopyrazole,
5-(2-methoxyphenyl)-3-(4-phenylpiperazinyl)
carbonylaminopyrazole,
5-(3,4-dichlorophenyl)-3-(4-phenylpiperazinyl)
carbonylaminopyrazole,
5-(4-bromophenyl)-3-(4-phenylpiperazinyl)
carbonylaminopyrazole,
5-(3-chlorophenyl)-3-(4-phenylpiperazinyl)
carbonylaminopyrazole,
5-phenyl-3-(4-phenylpiperazinyl)carbonylaminopyrazole,
5-(4-dimethylaminophenyl)-3-(4-phenylpiperazinyl)
carbonylaminopyrazole,
5-(3-dimethylaminophenyl)-3-(4-phenylpiperazinyl)
carbonylaminopyrazole,
5 (3,4-dimethoxyphenyl)-3-(4-phenylpiperazinyl)
carbonylaminopyrazole,
5-(4-isopropoxyphenyl)-3-(4-phenylpiperazinyl)
carbonylaminopyrazole,
5-(4-ethoxyphenyl)-3-(4-phenylpiperazinyl)
carbonylaminopyrazole,
5-(3-bromophenyl)-3-(4-phenylpiperazinyl)
carbonylaminopyrazole,
3-[4-(3-chlorophenyl)piperazinyl]carbonylamino-5-(4-
methoxyphenyl)pyrazole,
3-[4-(3-chlorophenyl)piperazinyl]carbonylamino-5-(3,4-
dimethoxyphenyl)pyrazole,
5-(2-chlorophenyl)-3-(4-phenylpiperazinyl)
carbonylaminopyrazole,
5-(4-methylthiophenyl)-3-(4-phenylpiperazinyl)
carbonylaminopyrazole,
5-(3,4-methylenedioxyphenyl)-3-(4-phenylpiperazinyl)
carbonylaminopyrazole,
3-(4-phenylpiperazinyl)carbonylamino-5-(4-pyridyl)
pyrazole,
5-(4-methoxyphenyl)-3-methyl[2-(methylphenylamino)
ethyl]aminocarbonylaminopyrazole,
5-(3-methoxyphenyl)-3-(4-phenylpiperazinyl)
carbonylaminopyrazole,
5-(4-methoxyphenyl)-3-(2-methyl-4-phenylpiperazinyl)
carbonylaminopyrazole,
5-(4-methoxyphenyl)-3-[2-(phenylamino)ethyl]
aminocarbonylaminopyrazole,
5-(4-biphenylyl)-3-(4-phenylpiperazinyl)
carbonylaminopyrazole,
5-(3-dimethylamino-4-methoxyphenyl)-3-(4-
phenylpiperazinyl)-carbonylaminopyrazole,
3-(4-hydroxy-4-phenylpiperidino)carbonylamino-5-(4-
methoxyphenyl)pyrazole,
5-(4-methoxyphenyl)-3-(4-phenyl-1,2,3,6-
tetrahydropyridin-1-yl)carbonylaminopyrazole,
5-(4-methoxyphenyl)-3-(4-phenylpiperidino)
carbonylaminopyrazole,
5-(4-methoxyphenyl)-3-(4-phenylhomopiperazinyl)
carbonyaminopyrazole.

Next, a process for the preparation of the compound of the present invention is described below.

The compound [I] of the present invention can be prepared, for example, by the following process or the method as shown in Examples. However, the process for the preparation of the compound [I] of the present invention is not limited thereto.

Process

The compound represented by the general formula [I] can be prepared by reacting a compound represented by the general formula [II]:

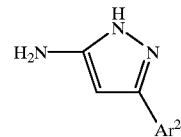

[II]

wherein $Ar^2$ is as defined above, with a compound represented by the general formula [III]:

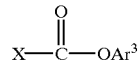

[III]

wherein $Ar^3$ represents a phenyl group which may be substituted with a halogen atom or a nitro group; and X represents a halogen atom, to obtain a compound represented by the general formula [IV]:

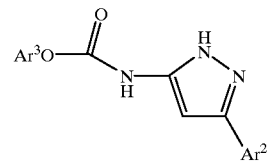

[IV]

wherein $Ar^2$ and $Ar^3$ are as defined above, and then reacting the compound [IV] with a compound represented by the general formula [V]:

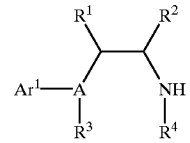

[V]

wherein A, $Ar^1$, $R^1$, $R^2$, $R^3$ and $R^4$ are as defined above.

The reaction of the compound of the general formula [II] with the compound of the general formula [III] is generally carried out using 0.5 mole to excess moles, preferably 1 mole to 1.5 moles, of the compound of the general formula [III] with respect to 1 mole of the compound of the general formula [II].

The reaction is generally carried out in an inert solvent, and preferred examples of said inert solvent include methylene chloride, chloroform, tetrahydrofuran, ethyl ether, benzene, toluene and dimethylformamide and a mixture thereof.

Also, it is desirable to carry out the reaction in the presence of a base, and examples of said base to be used include an organic base such as triethylamine, diisopropylethylamine, pyridine or 4-dimethylaminopyridine, or an inorganic base such as sodium hydroxide, potassium hydroxide, sodium carbonate, potassium carbonate or sodium bicarbonate.

It is desirable to use said base generally in an amount of from 1 mole to excess moles with respect to 1 mole of the compound of the general formula [II]. When said base is liquid, it can be used as both a solvent and a base.

The reaction temperature is generally within the range of from −78° C. to 100° C., preferably from −20° C. to 50° C.

The reaction time is generally within the range of from 5 minutes to 7 days, preferably from 30 minutes to 24 hours.

The reaction of the compound of the general formula [IV] with the compound of the general formula [V] is generally carried out using 1 mole to excess moles, preferably 1 mole to 1.5 moles, of the compound of the general formula [V] with respect to 1 mole of the compound of the general formula [IV] optionally after the isolation of the compound of the general formula [IV] obtained in the above reaction.

The reaction is generally carried out in an inert solvent, and preferred examples of said inert solvent include methylene chloride, chloroform, tetrahydrofuran and dimethylformamide and a mixture thereof.

Also, it is desirable to carry out the reaction in the presence of a base, and preferred examples of said base to be used include triethylamine and diisopropylethylamine.

Said base is generally used in an amount of from 1 mole to excess moles, preferably 1 mole to 5 moles, with respect to 1 mole of the compound of the general formula [IV].

The reaction temperature is generally within the range of from −30° C. to 200° C., preferably from 20° C. to 100° C.

The reaction time is generally within the range of from 5 minutes to 7 days, preferably from 30 minutes to 24 hours.

The objective compound in each step can be easily isolated and purified by any conventional separation methods. Examples of such methods include solvent extraction, recrystallization, column chromatography and preparative thin layer chromatography.

The compound represented by the general formula [I] can be converted into its pharmaceutically acceptable salt according to any conventional method and vice versa.

The compound of the general formula [II] to be used in the present invention is commercially available, or it can be prepared, for example, in accordance with the methods described in references such as Comprehensive Heterocyclic Chemistry, vol.5, edited by A. R. Katritzky, Pergamon Press (1984) or their modifications, or alternatively with the following process or the method as described in the reference examples.

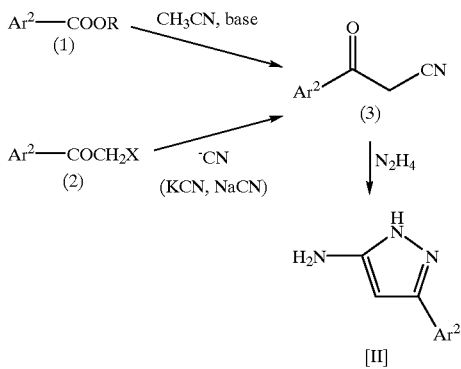

wherein R represents a lower alkyl group; and $Ar^2$ and X are as defined above.

According to this process, the compound of the general formula [II] can be prepared by reacting a compound represented by the general formula (1) with acetonitrile in the presence of any base to obtain a compound represented by the general formula (3), and subsequently reacting said compound (3) with hydrazine.

Conditions for the reaction of the compound (1) with acetonitrile vary depending on the nature of the base to be used.

For example, when n-butyllithium, lithium diisopropylamide or the like is used as said base, the reaction is generally carried out in any inert solvent such as tetrahydrofuran or ethyl ether at a temperature of from −78° C. to room temperature for a reaction period of from 30 minutes to 6 hours.

When sodium hydride or the like is used as said base, the reaction is generally carried out in an inert solvent such as tetrahydrofuran, ethyl ether or dimethylformamide at a temperature of from room temperature to 100° C. for a reaction period of from 1 hour to 6 hours.

The reaction of the compound (3) with hydrazine is generally carried out in an inert solvent such as ethanol, propanol, isoamyl alcohol, acetic acid, benzene, toluene or xylene or a mixture thereof, using hydrazine in an amount of from 0.5 mole to 10 moles, preferably from 1 mole to 1.5 moles, with respect to 1 mole of the compound (3).

The reaction temperature is generally from room temperature to the boiling point of the solvent to be used, preferably from 50° C. to the boiling point of the solvent to be used.

The reaction time is generally from 30 minutes to 7 days, preferably from 1 hour to 48 hours.

The hydrazine to be used in the reaction may be either anhydride or hydrate.

In addition, the compound of the general formula (3) can also be prepared by using a compound represented by the general formula (2) in stead of the compound represented by the general formula (1), and reacting it with a cyanide.

In this connection, the compound represented by the general formula (1) or (2) is commercially available or it can be prepared in accordance with known methods or their modifications which may be suitably combined if necessary.

The compound represented by the general formula [III] or [V] to be used in the present invention is commercially available or it can be prepared according to known methods or their modifications which may be suitably combined if necessary.

The usefulness of the compound of the present invention as a medicine is demonstrated by showing its antagonistic activity to NPY in the following pharmacological test examples.

PHARMACOLOGICAL TEST EXAMPLE 1

(Test of Inhibition of NPY Binding)

cDNA Sequence encoding a human NPY Y5 receptor [International Publication WO 96/16542] was cloned into expression vectors pcDNA3, pRc/RSV (manufactured by Invitrogen) and pCI-neo (manufactured by Promega). Using the cationic lipid method [see Proceedings of the National Academy of Science of the United States of America, vol.84, p.7413 (1987)], host cells COS-7, CHO and LM(tk-) (American Type Culture Collection) were transfected with the thus prepared expression vectors to obtain cells in which the NPY Y5 receptor had been expressed.

Each of the membrane preparations thus prepared from the cells in which the NPY Y5 receptor had been expressed was incubated together with each compound to be tested and 20,000 cpm of [$^{125}$I] peptide YY (manufactured by Amersham) at 25° C. for 2 hours in an assay buffer solution (25 mM HEPES buffer, pH 7.4, containing 10 mM magnesium chloride, 1 mM phenylmethylsulfonyl fluoride and 0.1% bacitracin) and then, the reaction mixture was filtered through a glass filter GF/C. After washing with 50 mM Tris buffer, pH 7.4, containing 0.3% BSA, radioactivity on the glass filter was measured using a gamma counter. Non-specific binding was measured in the presence of 1 μM of peptide YY to calculate a concentration of each compound tested which is needed to inhibit 50% of the specific binding of peptide YY ($IC_{50}$ value) [Fee Endocrinology, vol.131, p.2090 (1992)]. As the result, $IC_{50}$ value of the compound of Example 17 was calculated to be 27 nm.

As shown in the above, the compound of the present invention strongly inhibited the binding of the peptide YY (a homologue of NPY) to the NPY Y5 receptor.

PHARMACOLOGICAL TEST EXAMPLE 2

(Test of Inhibition of Feeding Behavior Induced by bPP)

Under pentobarbital anesthesia (single intraperitoneal injection of 50 mg/kg), a chronic guide cannula (outer diameter 0.8 mm; inner diameter 0.5 mm; length 10 mm) was stereotactically inserted in a right lateral cerebral ventricle of each of SD male rats (7 to 8-week-old, 200 to 300 g) and fixed using a dental resin. A tip of the guide cannula was positioned 0.9 mm behind a bregma, 1.2 mm at the right of a median line and in the depth of 1.5 mm from the brain surface. An inner needle was inserted such that its tip projected from the tip of the guide cannula by about 2 mm and arrived to a lateral cerebral ventricle. After a recovery period of about one week, a bovine pancreatic polypeptide (bpp, 5 μg/head/10 μl) was administered to the lateral cerebral ventricle. A compound to be tested was simultaneously administered as a mixture with bPP. Food intake during 2 hours from the administration was measured. In this connection, both bPP and the compound to be tested were administered after dissolving them in 50% propylene glycol.

The compound of the present invention significantly inhibits the increase in food intake induced by bPP (a homologue of NPY) simultaneously administered.

In consequence, the compound [I] of the present invention is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma, especially bulimia, obesity and diabetes.

The compound represented by the general formula [I] can be administered orally or parenterally and by formulating into any dosage forms suitable for such an administration, it can be used as an agent for the treatment of the diseases of circulatory organs such as hypertension, nephropathy, cardiopathy and angiospasm, the diseases of central nervous system such as bulimia, depression, epilepsy and dementia, the metabolic diseases such as obesity, diabetes and dysendocrisiasis, or glaucoma. In clinical use of the compound of the present invention, it is also possible to administer the compound after formulating it into various pharmaceutical preparations by adding any pharmaceutically acceptable additives). Examples of such additive include those which are generally used in the field of pharmaceutical preparations, such as gelatin, lactose, sucrose, titanium oxide, starch, crystalline cellulose, hydroxypropylmethyl cellulose, carboxymethyl cellulose, corn starch, microcrystalline wax, white soft paraffine, magnesium aluminate methasilicate, anhydrous calcium phosphate, citric acid, trisodium citrate, hydroxypropyl cellulose, sorbitol, sorbitan fatty acid ester, polysorbate, sucrose fatty acid ester, polyoxyethylene hydrogenated castor oil, polyvinyl pyrrolidone, magnesium stearate, light anhydrous silicic acid, talc, vegetable oil, benzyl alcohol, gum arabic, propylene glycol, polyalkylene glycol, cyclodextrin and hydroxypropyl cyclodextrin.

Examples of the dosage form to be formulated as a mixture with these additives include solid preparations such as tablet, capsule, granule, powder or suppository; and liquid preparations such as syrup, elixir or injection, which can be prepared in accordance with any conventional method in the field of pharmaceuticals. In this connection, in the case of a liquid preparation, it may be in a form which is dissolved or suspended in water or other suitable solvent when used. Also, particularly in the case of an injection, it may be dissolved or suspended in physiological saline or glucose solution if necessary or further mixed with buffer and/or preservative.

The pharmaceutical preparation may contain the compound of the present invention in an amount of from 1.0 to 100% by weight, preferably from 1.0 to 60% by weight, with respect to the total preparation. The pharmaceutical preparation may also contain any other therapeutically effective compounds.

When the compound of the present invention is, for example, clinically used, its dosage and the number of times of its administration vary depending on the sex, age, body weight and the conditions of each patient and the nature and ranges of the intended therapeutic effects and the like. When it is administered to an adult, it is desirable in general to orally administer in an amount of from 0.1 to 100 mg/kg per day by dividing the daily dose into 1 to several times per day, or to parenterally administer in an amount of from 0.001 to 10 mg/kg by dividing the daily dose into 1 to several times per day.

BEST MODE FOR CARRYING OUT THE INVENTION

The present invention is described further in detail with reference to the following examples, but the invention should in no way be restricted thereby.

EXAMPLE 1

Preparation of 5-(4-methoxyphenyl)-3-(4-phenylpiperazinyl)-carbonylaminopyrazole (1) Preparation of 5-(4-methoxyphenyl)-3-phenoxycarbonyl-aminopyrazole Phenyl chlorocarbonate (0.87 ml) was added to a solution of 3-amino-5-(4-methoxyphenyl)pyrazole (1.19 g) in pyridine (10 ml), and the mixture was stirred at room temperature for 6 hours. The reaction solution was partitioned between ethyl acetate (50 ml) and water (30 ml), and the organic layer was washed with 1 N hydrochloric acid (50 ml×2), saturated aqueous sodium bicarbonate (50 ml) and saturated brine (50 ml) and then dried over anhydrous magnesium sulfate. Then, the solvent was distilled away. The resulting residue was crystallized from ethyl acetate/hexane to obtain the title compound (0.95 g) as pale yellow crystals (melting point: 286–291° C.).

(2) Preparation of 5-(4-methoxyphenyl)-3-(4-phenylpiperazinyl)-carbonylaminopyrazole A mixture of 5-(4-methoxyphenyl)-3-phenoxycarbonylaminopyrazole (93 mg), 1-phenylpiperazine (54 mg) and triethylamine (91 mg) was heated under reflux for 2 hours in chloroform (3 ml). After the reaction solution was allowed to cool, ethyl ether (3 ml)

was added thereto, and the thus precipitated crystals were collected by filtration and dried to obtain the title compound (103 mg) as colorless crystals (melting point: 235–245° C.).

Each of compounds of Examples 2 to 32 was obtained in the same manner as that described in Example 1 except that the starting materials used in Example 1 were replaced with appropriate starting materials corresponding to the desired compound.

EXAMPLE 2
5-(4-chlorophenyl)-3-(4-phenylpiperazinyl) carbonylaminopyrazole
melting point: 245–248° C.

EXAMPLE 3
5-(2-methylphenyl)-3-(4-phenylpiperazinyl) carbonylaminopyrazole
melting point: 123–127° C.

EXAMPLE 4
5-(3-methylphenyl)-3-(4-phenylpiperazinyl) carbonylaminopyrazole
melting point: 140–141° C.

EXAMPLE 5
5-(4-methylphenyl)-3-(4-phenylpiperazinyl) carbonylaminopyrazole
melting point: 233–235° C.

EXAMPLE 6
5-(2-methoxyphenyl)-3-(4-phenylpiperazinyl) carbonylaminopyrazole
melting point: 183–185° C.

EXAMPLE 7
5-(3,4-dichlorophenyl)-3-(4-phenylpiperazinyl)-carbonylaminopyrazole
melting point: 252–254° C.

EXAMPLE 8
5-(4-bromophenyl)-3-(4-phenylpiperazinyl) carbonylaminopyrazole
melting point: 250–252° C.

EXAMPLE 9
5-(3-chlorophenyl)-3-(4-phenylpiperazinyl) carbonylaminopyrazole
melting point: 226–228° C.

EXAMPLE 10
5-phenyl-3-(4-phenylpiperazinyl)carbonylaminopyrazole
melting point: 232° C.

EXAMPLE 11
5-(4-dimethylaminophenyl)-3-(4-phenylpiperazinyl) carbonylaminopyrazole
melting point: 242–246° C.

EXAMPLE 12
5-(3-dimethylaminophenyl)-3-(4-phenylpiperazinyl) carbonylaminopyrazole
melting point: 155–163° C. (dihydrochloride)

EXAMPLE 13
5-(3,4-dimethoxyphenyl)-3-(4-phenylpiperazinyl) carbonylaminopyrazole
melting point: 116–119° C.

EXAMPLE 14
5-(4-isopropoxyphenyl)-3-(4-phenylpiperazinyl) carbonylaminopyrazole
melting point: 245–246° C.

EXAMPLE 15
5-(4-ethoxyphenyl)-3-(4-phenylpiperazinyl) carbonylaminopyrazole
melting point: 231–235° C.

EXAMPLE 16
5-(3-bromophenyl)-3-(4-phenylpiperazinyl) carbonylaminopyrazole
melting point: 208–209° C.

EXAMPLE 17
3-[4-(3-chlorophenyl)piperazinyl]carbonylamino-5-(4-methoxyphenyl)pyrazole
melting point: 214–216° C.

EXAMPLE 18
3-[4-(3-chlorophenyl)piperazinyl]carbonylamino-5-(3,4-dimethoxyphenyl)pyrazole
melting point: 115–117° C.

EXAMPLE 19
5-(2-chlorophenyl)-3-(4-phenylpiperazinyl) carbonylaminopyrazole
melting point: 168–169° C.

EXAMPLE 20
5-(4-methylthiophenyl)-3-(4-phenylpiperazinyl) carbonylaminopyrazole
melting point: 253–258° C.

EXAMPLE 21
5-(3,4-methylenedioxyphenyl)-3-(4-phenylpiperazinyl) carbonylaminopyrazole
melting point: 223–228° C.

EXAMPLE 22
3-(4-phenylpiperazinyl)carbonylamino-5-(4-pyridyl) pyrazole
melting point: 249–255° C.

EXAMPLE 23
5-(4-methoxyphenyl)-3-methyl[2-(methylphenylamino) ethyl]aminocarbonylaminopyrazole
$^1$H-NMR(CDCl$_3$) δ: 2.99 (3H, s), 3.01 (3H, s), 3.56 (4H, S), 3.83 (3H, s), 6.23 (1H, brs), 6.75–6.85 (3H, m), 6.92 (2H, d, J=8.8 Hz), 7.22–7.32 (2H, m), 7.45 (1H, brs), 7.54 (2H, d, J=8.8 Hz)

EXAMPLE 24
5-(3-methoxyphenyl)-3-(4-phenylpiperazinyl) carbonylaminopyrazole
melting point: 172–174° C.

EXAMPLE 25
5-(4-methoxyphenyl)-3-(2-methyl-4-phenylpiperazinyl) carbonylaminopyrazole
melting point: 111–116° C.

EXAMPLE 26
5-(4-methoxyphenyl)-3-[2-(phenylamino)ethyl] aminocarbonylaminopyrazole
melting point: 183–184° C.

EXAMPLE 27
5-(4-biphenylyl)-3-(4-phenylpiperazinyl) carbonylaminopyrazole
melting point: 274–276° C.

EXAMPLE 28
5-(3-dimethylamino-4-methoxyphenyl)-3-(4-phenylpiperazinyl)-carbonylaminopyrazole
melting point: 233–235° C.

EXAMPLE 29
3-(4-hydroxy-4-phenylpiperidino)carbonylamino-5-(4-methoxyphenyl)pyrazole
melting point: 234–236° C.

EXAMPLE 30
5-(4-methoxyphenyl)-3-(4-phenyl-1,2,3,6-tetrahydropyridin-1-yl)carbonylaminopyrazole
melting point: 232–235° C.

EXAMPLE 31
5-(4-methoxyphenyl)-3-(4-phenylpiperidino) carbonylaminopyrazole
melting point: 205–208° C.

EXAMPLE 32
5-(4-methoxyphenyl)-3-(4-phenylhomopiperazinyl) carbonylaminopyrazole
melting point: 115–123° C.

REFERENCE EXAMPLE 1
Preparation of 3-amino-5-(3,4-dimethoxyphenyl)pyrazole
(1) Preparation of 3,4-dimethoxybenzoylacetonitrile Dry acetonitrile (1.8 ml) was added to a solution of n-butyl lithium (a 2.5M solution in hexane, 13.8 ml) in dry THF (30 ml) at −78° C., and the mixture was stirred at the same temperature for 1 hour. To the mixture was added a solution of methyl 3,4-dimethoxybenzoate (6.42 g) in dry THF (15 ml), and the mixture was stirred at −78° C. for 3 hours and then at room temperature for 1 hour. After adding water (100 ml), the reaction solution was extracted with ethyl ether (100 ml). After the aqueous layer was acidified with 6 N hydrochloric acid, it was extracted with ethyl acetate (200 ml×3). The organic layers were combined, washed with saturated brine and then dried over anhydrous sodium sulfate. Then the solvent was distilled away under a reduced pressure. The resulting residue was crystallized from ethyl acetate/hexane to obtain the title compound (3.6 g) as pale yellow crystals.

$^1$H-NMR (CDCl$_3$) δ: 3.95 (3H, s), 3.97 (3H, s), 4.03 (2H, s), 6.92 (1H, d, J=9.0 Hz), 7.49 (1H, d, J=9.0 Hz), 7.51 (1H, s)

(2) Preparation of 3-amino-5-(3,4-dimethoxyphenyl) pyrazole 3,4-Dimethoxybenzoylacetonitrile (3.6 g) was dissolved in ethanol (20 ml), to which was subsequently added hydrazine monohydrate (0.87 ml) under cooling with ice. The mixture was heated under ref lux for 7 hours, allowed to cool and then the solvent was distilled away under a reduced pressure. The resulting residue was recrystallized from ethyl acetate to obtain the title compound (2.92 g) as colorless crystals (melting point: 124–125° C.).

Each of the following compounds was obtained in the same manner as that described in the above except that methyl 3,4-dimethoxybenzoate used in the above reaction was replaced with an appropriate compound corresponding to the desired compound.

3-amino-5-(3-chlorophenyl)pyrazole
melting point: 103–104° C.;
3-amino-5-(3,4-dichlorophenyl)pyrazole
melting point: 169–170° C.;
3-amino-5-(4-dimethylaminophenyl)pyrazole
melting point: 215–218° C. (decomposition);
3-amino-5-(3-dimethylaminophenyl)pyrazole (dihydrochloride)
melting point: 195–200° C. (decomposition);
3-amino-5-(4-isopropoxyphenyl)pyrazole
melting point: 160–165° C.;
3-amino-5-(3-bromophenyl)pyrazole
melting point: 126–130° C.;
3-amino-5-(4-methylthiophenyl)pyrazole
melting point: 150–156° C.;
3-amino-5-(3,4-methylenedioxyphenyl)pyrazole
melting point: 134–136° C.;
3-amino-5-(4-biphenylyl)pyrazole
melting point: 256–258° C.;
3-amino-5-(3-dimethylamino-4-methoxyphenyl)pyrazole
melting point: 158–160° C.

INDUSTRIAL APPLICABILITY

Since the compound of the present invention has an antagonistic action to NPY, it is useful as an agent for the treatment of various diseases associated with NPY, for example, diseases of circulatory organs such as hypertension nephropathy, cardiopathy and angiospasm, diseases of central nervous system such as bulimia, depressions epilepsy and dementia metabolic diseases such as obesity, diabetes and dysendocrisiasis, or glaucoma.

We claim:

1. A compound represented by the general formula [I]:

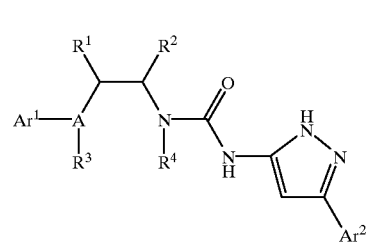

wherein A represents a nitrogen atom or a group represented by C—R$^5$; Ar$^1$ represents an aryl group which may have a substituent selected from the group consisting of a halogen atom and lower alkyl and lower haloalkyl groups; Ar$^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; R$^1$ represents a hydrogen atom, a lower alkyl group or a bond formed by linking to R$^5$; R$^2$ represents a hydrogen atom or a lower alkyl group; R$^3$ and R$^4$ may be the same or different and each represents a hydrogen atom or a lower alkyl group, or R$^3$ and R$^4$ are linked to each other to form an alkylene group containing 2 to 4 carbon atoms which may have a lower alkyl group; and R$^5$ represents a hydrogen atom or a hydroxyl, lower alkyl or lower alkoxy group or a bond formed by linking to R$^1$, or a salt thereof.

2. The compound as claimed in claim 1 wherein the aryl group as Ar$^1$ is a phenyl group.

3. The compound as claimed in claim 1 wherein the aryl group as Ar$^2$ is a phenyl group.

4. The compound as claimed in claim 1 wherein the heteroaryl group as Ar$^2$ is a pyridyl group.

5. The compound as claimed in claim 1 wherein $R^1$ and $R^2$ are hydrogen atoms.

6. The compound as claimed in claim 1 wherein $R^3$ and $R^4$ which may be the same or different are each a lower alkyl group.

7. The compound as claimed in claim 1 wherein $R^3$ and $R^4$ are linked to each other to form an alkylene group containing 2 to 4 carbon atoms which may have a lower alkyl group.

8. The compound as claimed in claim 7 wherein the alkylene group contains 2 carbon atoms.

9. The compound as claimed in claim 1 which is 5-(4-methoxyphenyl)-3-(4-phenylpiperazinyl)carbonylaminopyrazole, 5-(4-chlorophenyl)-3-(4-phenylpiperazinyl)carbonylaminopyrazole, 5-(2-methylphenyl)-3-(4-phenylpiperazinyl)carbonylaminopyrazole, 5-(3-methylphenyl)-3-(4-phenylpiperazinyl)carbonylaminopyrazole, 5-(4-methylphenyl)-3-(4-phenylpiperazinyl)carbonylaminopyrazole, 5-(2-methoxyphenyl)-3-(4-phenylpiperazinyl)carbonylaminopyrazole, 5-(3,4-dichlorophenyl)-3-(4-phenylpiperazinyl)carbonylaminopyrazole, 5-(4-bromophenyl)-3-(4-phenylpiperazinyl)carbonylaminopyrazole, 5-(3-chlorophenyl)-3-(4-phenylpiperazinyl)carbonylaminopyrazole, 5-phenyl-3-(4-phenylpiperazinyl)carbonylaminopyrazole, 5-(4-dimethylaminophenyl)-3-(4-phenylpiperazinyl)carbonylaminopyrazole, 5-(3-dimethylaminophenyl)-3-(4-phenylpiperazinyl)carbonylaminopyrazole, 5-(3,4-dimethoxyphenyl)-3-(4-phenylpiperazinyl)carbonylaminopyrazole, 5-(4-isopropoxyphenyl)-3-(4-phenylpiperazinyl)carbonylaminopyrazole, 5-(4-ethoxyphenyl)-3-(4-phenylpiperazinyl)carbonylaminopyrazole, 5-(3-bromophenyl)-3-(4-phenylpiperazinyl)carbonylaminopyrazole, 3-[4-(3-chlorophenyl)piperazinyl]carbonylamino-5-(4-methoxyphenyl)pyrazole, 3-[4-(3-chlorophenyl)piperazinyl]carbonylamino-5-(3,4-dimethoxyphenyl)pyrazole, 5-(2-chlorophenyl)-3-(4-phenylpiperazinyl)carbonylaminopyrazole, 5-(4-methylthiophenyl)-3-(4-phenylpiperazinyl)carbonylaminopyrazole, 5-(3,4-methylenedioxyphenyl)-3-(4-phenylpiperazinyl)carbonylaminopyrazole, 3-(4-phenylpiperazinyl)carbonylamino-5-(4-pyridyl)pyrazole, 5-(4-methoxyphenyl)-3-methyl[2-(methylphenylamino)ethyl]-aminocarbonylaminopyrazole, 5-(3-methoxyphenyl)-3-(4-phenylpiperazinyl)carbonylaminopyrazole, 5-(4-methoxyphenyl)-3-(2-methyl-4-phenylpiperazinyl)carbonylaminopyrazole, 5-(4-methoxyphenyl)-3-[2-(phenylamino)ethyl]aminocarbonylaminopyrazole, 5-(4-biphenylyl)-3-(4-phenylpiperazinyl)carbonylaminopyrazole, 5-(3-dimethylamino-4-methoxyphenyl)-3-(4-phenylpiperazinyl)-carbonylaminopyrazole, 3-(4-hydroxy-4-phenylpiperidino)carbonylamino-5-(4-methoxyphenyl)pyrazole, 5-(4-methoxyphenyl)-3-(4-phenyl-1,2,3,6-tetrahydropyridin-1-yl)carbonylaminopyrazole, 5-(4-methoxyphenyl)-3-(4-phenylpiperidino)carbonylaminopyrazole, or 5-(4-methoxyphenyl)-3-(4-phenylhomopiperazinyl)carbonylaminopyrazole.

10. A method for preparing a compound represented by the general formula [I]:

[I]

wherein A represents a nitrogen atom or a group represented by C—$R^5$; $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ represents a hydrogen atom, a lower alkyl group or a bond formed by linking to $R^5$; $R^2$ represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a hydroxyl, lower alkyl or lower alkoxy group or a bond formed by linking to $R^1$, which comprises reacting a compound represented by the general formula [II]:

[II]

wherein $Ar^2$ is as defined above, with a compound represented by the general formula [III]:

[III]

$$X-\overset{O}{\underset{\|}{C}}-OAr^3$$

wherein $Ar^3$ represents a phenyl group which may be substituted with a halogen atom or a nitro group; and x represents a halogen atom, to obtain a compound represented by the general formula [IV]:

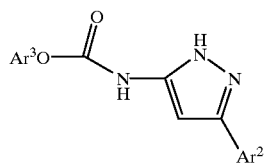

[IV]

wherein $Ar^2$ and $Ar^3$ are as defined above, and then reacting the compound [IV] with a compound represented by the general formula [V]:

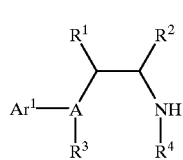

[V]

wherein A, $Ar^1$, $R^1$, $R^2$, $R^3$ and $R^4$ are as defined above.

11. A neuropeptide Y receptor antagonist comprising a compound represented by the general formula [I]:

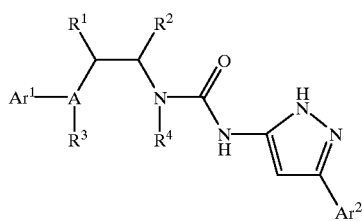

[I]

wherein A represents a nitrogen atom or a group represented by C—$R^5$; $Ar^1$ represents an aryl group which may have a substituent selected from the group consisting of a halogen atom and lower alkyl and lower haloalkyl groups; $Ar^2$ represents an aryl or heteroaryl group which may have a substituent selected from the group consisting of a halogen atom and lower alkyl, lower alkenyl, lower haloalkyl, lower alkoxy lower alkylthio, lower alkylamino, lower dialkylamino and aryl groups; $R^1$ represents a hydrogen atom, a lower alkyl group or a bond formed by linking to $R^5$; $R^2$ represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a hydroxyl, lower alkyl or lower alkoxy group or a bond formed by linking to $R^1$, or a salt thereof as an active ingredient.

12. An agent for the treatment of bulimia, obesity or diabetes comprising a compound represented by the general formula [I];

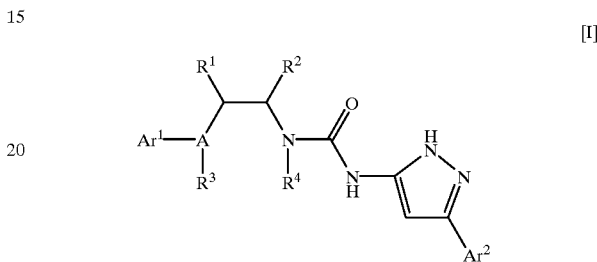

[I]

wherein A represents a nitrogen atom or a group represented by C—$R^5$; $Ar^1$ represents an aryl group which may have a substituent selected from the group consisting of a halogen atom and lower alkyl, lower haloalkyl groups; $Ar^2$ represents an aryl or heteroaryl group which may have a substituent selected from the group consisting of a halogen atom and lower alkyl, lower alkenyl, lower haloalkyl, lower alkoxy, lower alkylthio, lower alkylamino, lower dialkylamino and aryl groups; $R^1$ represents a hydrogen atom, a lower alkyl group or a bond formed by linking to $R^5$; $R^2$ represents a hydrogen atom or a lower alkyl group; $R^3$ and $R^4$ may be the same or different and each represents a hydrogen atom or a lower alkyl group, or $R^3$ and $R^4$ are linked to each other to form an alkylene group containing 2 to 4 carbon atoms which may have a lower alkyl group; and $R^5$ represents a hydrogen atom or a hydroxyl, lower alkyl or lower alkoxy group or a bond by linking to $R^1$, or a salt thereof as an active ingredient.

* * * * *